US005122156A

United States Patent [19]
Granger et al.

[11] Patent Number: 5,122,156
[45] Date of Patent: Jun. 16, 1992

[54] APPARATUS FOR SECUREMENT AND ATTACHMENT OF BODY ORGANS

[75] Inventors: Richard N. Granger, Huntington; Herbert W. Korthoff, Westport, both of Conn.

[73] Assignee: United States Surgical Corporation, Norwalk, Conn.

[21] Appl. No.: 628,189

[22] Filed: Dec. 14, 1990

[51] Int. Cl.⁵ .............................................. A61B 17/00
[52] U.S. Cl. ................................. 606/219; 227/179; 227/180; 227/19
[58] Field of Search ................. 606/219; 227/175–180, 227/19

[56] References Cited
U.S. PATENT DOCUMENTS

| | | | |
|---|---|---|---|
| 4.598.712 | 7/1986 | Rebuffat et al. | |
| 4.603.693 | 8/1986 | Conta et al. | 606/180 |
| 4.606.343 | 8/1986 | Conta et al. | 606/179 |
| 4.646.745 | 3/1987 | Noiles | 227/19 |
| 4.681.108 | 7/1987 | Rosati et al. | 227/213 |
| 4.752.024 | 6/1988 | Green et al. | 227/19 |
| 4.776.506 | 10/1988 | Green | 227/19 |
| 4.821.939 | 4/1989 | Green | 227/180 |
| 4.893.622 | 1/1990 | Green et al. | |
| 4.907.591 | 3/1990 | Vasconcellos et al. | 606/154 |
| 4.917.114 | 4/1990 | Green et al. | 227/179 |
| 4.931.057 | 6/1990 | Cummings et al. | 606/153 |

OTHER PUBLICATIONS

"Informative Booklet for an Auto Suture, Surgical Stapling Instrument," United States Surgical Corporation, 1984.

Primary Examiner—Stephen C. Pellegrino
Assistant Examiner—Gary Jackson
Attorney, Agent, or Firm—Thomas R. Bremer; Rocco S. Barrese; Peter G. Dilworth

[57] ABSTRACT

An apparatus and method is disclosed for performing circular anastomosis on body portions, such body portions preferably include at least one tubular organ such as intestines, colons, or the like. The apparatus includes an annular crown-like structure which includes a plurality of elongated sharp resilient members positioned and adapted to pierce and secure the tubular body part in position for attachment to the other body part. An anvil for providing closure in such circular anastomosis and a method of performing such circular anastomosis are also disclosed. A unique anvil for performing such procedures with staples is also disclosed.

30 Claims, 7 Drawing Sheets

APPARATUS FOR SECUREMENT AND ATTACHMENT OF BODY ORGANS

BACKGROUND OF THE INVENTION

1. Field of the Invention

This invention relates to an apparatus for attaching hollow tubular body portions such as for anastomosis of intestinal tissue.

2. Description of the Prior Art

The present invention is capable of use with all types of devices utilized for attaching tubular body portions. Such devices may include staplers, fastener appliers and fixtures utilized in combination with sutures for temporarily securing the hollow organs in position for suturing. For convenience of the present description, reference will be made to staples and staplers; however, all types of fastener devices and securement techniques are contemplated For example, such devices include appliers for two-part absorbable fasteners, or even a fixture to secure the hollow organs in position for attaching by sutures.

Fastening of separate body parts by circular anastomosis is well known. Generally, the two body parts are attached along a circular path and the tissue within the circular path is removed to clear a passage therewithin. Such circular anastomosis is particularly utilized with tubular organs such as intestines, colons, etc. which involves the attachment of two separate tubular body portions by means of a stapling apparatus after removal of a defective or diseased section. The tubes are connected by a circular array of staples and the overlapping tissue is then cut away to free the tubular passages.

The apparatus used generally includes a staple holding component and an anvil component mounted on a common shaft and movable away from each other for securement of the tubular body portions prior to fastening. Each end of the body portions to be attached is secured to the respective stapler component by a well-known purse string stitch to cause the tubular body portion to tighten and to remain on the apparatus in position for permanent attachment with the staples. Thereafter the staple containing member and the anvil member are brought together and the hollow tubular sections are attached by a plurality of circular rows of staples or fasteners which are fired by the staple containing component. In some instances, a system of clamping rings is used.

After the attachment is completed, the portions of tubular body organs which are folded inwardly are removed by a circular knife to once again clear the organ for passage of bulk matter.

Certain instances require attachment of a single tubular organ to a non-tubular body portion in which case the circular array of staples is utilized while the purse string stitch technique is utilized on the tubular organ.

The purse string stitch procedure which is utilized to temporarily secure the hollow tubular body parts on the fastening apparatus has been found to require additional, often excessive, time and causes additional trauma to the patient. Further, it has been found to unnecessarily delay the attachment procedure. The present invention relates to an apparatus which avoids these difficulties by providing a relatively quick simple device for temporarily securing the body parts in preparation for attachment procedures and for cutting away the portions of the body parts within the circular array of staples.

SUMMARY OF THE INVENTION

In combination with an apparatus for performing circular anastomosis of first and second body portions wherein a first fastening member is adapted to support a first body portion and a second fastening member is adapted to cooperate with the first fastening member to attach the first body portion to the second body portion, which comprises body tissue holding member positionable on the first fastening member and having a plurality of sharp tipped members positioned and oriented to pierce portions of the first body portion in a manner to secure the first body portion in position for attachment to said second body portion.

In particular, the invention relates to an apparatus for performing circular anastomosis of first and second body portions wherein a proximal fastening member is adapted to support a first body portion and a distal member is adapted to cooperate with the proximal fastening member to attach the body portions by circular anastomosis. The improvement comprises a first member positionable on the proximal member and having a plurality of generally sharp tipped members facing distally for securing the first body portion to retain the body portion in position for attachment to the other body portion and a second member positionable on the cooperating distal fastening member and having a plurality of sharp tipped members facing the proximal direction for securing the second body portion to retain the second body portion in position for attachment to the first body portion by circular anastomosis.

Generally stated, the invention relates to an apparatus for performing circular anastomosis at a location remote from the location at which the instrument is manipulated, which comprises an elongated member having opposite distal and proximal ends, with means located at the distal end of the elongated member for performing the surgical fastening procedure. The fastening means has proximal and distal fastening components arranged to be positioned within the respective opposite end portions of generally tubular shaped body portions to be fastened and to cooperate with each other for applying a circular array of staples or fasteners for attaching the generally tubular body portions. Means is attached to the distal fastening member in general concentric alignment therewith and has a plurality of sharp tipped members facing the proximal direction and positioned in a generally circular array, the sharp tipped members being adapted to penetrate and secure for fastening a tubular body portion positioned about the distal fastening member to maintain the body portion in position for attachment by circular anastomosis to the opposite body portion. Means is attached to the proximal fastening member in general concentric alignment therewith and has a plurality of sharp tipped members facing the distal direction and positioned in a generally circular array. The sharp tipped members are adapted to penetrate and secure for fastening a tubular body portion positioned about the proximal fastening member to maintain the body portion in position for circular attachment to the opposite body portion.

Preferably, the apparatus for attaching the tubular body portions is a surgical stapler and the first member is a crown-like member having a plurality of arcuately shaped barbed elongated members extending from a generally annular shaped base member. The crown-like member is preferably stamped from resilient stainless steel.

The apparatus includes a second crown-like member having a plurality of barbed elongated members extending from a generally circular shaped base member and stamped from resilient stainless steel. The second crown-like member is affixed to an anvil of a circular fastening apparatus while the first crown-like member is affixed to the staple holding and firing component. One crown-like member is of greater diameter than the other.

The first and second crown-like devices are dimensioned to be positioned adjacent each other within the tubular body organs (i.e. intestine, colon, etc.) in adjacent relation. When the staple components are brought together and fired, the smaller of the crown-like members enters the larger crown-like member such that the elongated spear-like members of each member are in concentric relation. The spear-like members continue to snag the excess overlapped tissue for removal with the fastener device. A circular knife which forms part of the apparatus cuts the excess tissue at the same time.

The crown-like devices of the present invention are structured for use with circular staplers, circular (two-part) fasteners or the like. Another use contemplated is a jig or fixture adapted to temporarily secure the hollow body parts for permanent attachment by any means including suturing. Further, the device may be utilized to secure several non-tubular members in position for attachment.

A method is disclosed for securement of a generally tubular body portion for attachment to a second body portion wherein a first fastener member and a second fastener member are adapted to cooperate with each other to attach the body portions by circular anastomosis, comprising positioning a crown-like member a first of the fastener members to secure the tubular body portion thereon for attachment to the other body portion, the crown-like member having an annular base member and a plurality of sharp spear-like members extending in an annular array from the base member toward said other fastening member and generally parallel to the central longitudinal axis of said fastening members. The method comprises positioning the tubular body portion over the first fastening member and folding an end portion over the crown-like member in a manner to cause the sharp spear-like members to pierce the tubular body portion to secure the body portion in position for attachment to the second body portion, and attaching the first tubular body portion to the second body portion.

The invention generally relates to a method for securement of hollow body parts in preparation for permanent attachment by staples, fasteners, retaining rings, sutures or the like comprising providing a first crown-like member having an annular base member and a plurality of sharp spear-like members extending in an annular array from the base member and generally parallel to a central longitudinal axis extending therethrough, mounting the crown-like member and support means and inserting the support means into an end portion of a first hollow body part, and providing a second a crown-like member on the support means. The second crown-like member has an annular base member and a plurality of sharp spear-like members extending in an annular array from the base member and generally parallel to the central longitudinal axis, the spear-like members facing a direction opposite the spear-like members of the first crown-like member.

According to the method the second crown-like member is inserted into the opposite open end portion of a second hollow body part to be attached to the first hollow body part, and the end portion of the first hollow body part is folded over the sharp end portions of the spear-like members of the first crown-like member to cause the spear-like members to penetrate marginal end portions of the hollow body part in a manner to secure the marginal end portion of the hollow part in position for permanent attachment to the second hollow body part. The end portion of the second hollow body part is folded over the sharp end portions of the spear-like members of the second crown-like member to cause the spear-like members to penetrate marginal end portions of the second hollow body portion in a manner to secure the marginal end portion thereof for permanent attachment to the first hollow body part.

The invention also relates to an anvil for providing closure to staples applied by a circular staple applying apparatus, the staples being applied in a circular array and the anvil having a plurality of lands correspondingly positioned to receive and close the staples. The improvement in combination therewith comprises a crown-like member having an annular base member formed of a resilient sheet steel and having a plurality of elongated sharp spear-like members extending from the annular base member and integral therewith, the resilient spear-like members being generally curved inwardly toward the longitudinal axis thereof from the base member to the sharp tips at the free ends thereof to facilitate piercing free end portions of a hollow body part in which the crown-like member is inserted for securing the body part in position in overlapping relation to the anvil staple closure lands for permanent staple attachment of the hollow body part to an opposite body part.

BRIEF DESCRIPTION OF THE DRAWINGS

Preferred embodiments of the invention are described hereinbelow with reference to the drawings wherein.

DETAILED DESCRIPTION OF THE PREFERRED EMBODIMENTS

Figure 1:
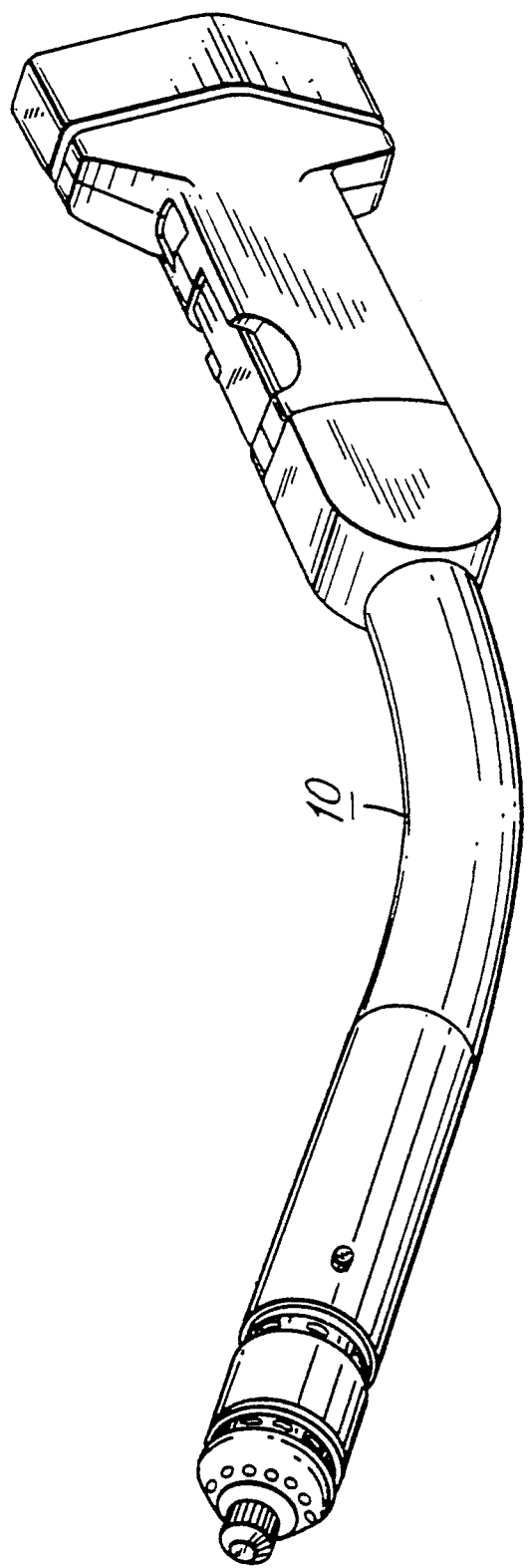
FIG. 1 is a perspective view of an exemplary powered stapling apparatus for attaching tubular body portions which utilized the purse string securement procedure.

Referring initially to FIG. 1, there is illustrated an apparatus 10 for stapling hollow tubular body organs as by circular anastomosis of intestines, colons, or the like. The apparatus may be utilized to attach two tubular body parts or one tubular body part to a non-tubular body part by circular anastomosis. Further, the apparatus may be utilized to attach two non-tubular body parts by staples, two-part absorbable fasteners, compression rings, etc.

Such apparatus 10 is disclosed and claimed in U.S. Pat. No. 4,606,343, issued Aug. 19, 1986, which is incorporated herein by reference herein and made a part of this disclosure. This apparatus is a powered stapler for anastomosis of hollow body organs such as intestines, colons, etc. Other such devices are disclosed in the following U.S patents which are also incorporated by reference herein and made a part of this disclosure: U.S. Pat. No. 4,646,745, issued Mar. 3, 1987; U.S. Pat. No. 4,893,622, issued Jan. 16, 1990; U.S. Pat. No. 4,776,506, issued Oct. 11, 1988; U.S. Pat. No. 4,603,693, issued Aug. 5, 1986; U.S. Pat. No. 4,752,024, issued Jun. 21, 1988; U.S. Pat. No. 4,681,108, issued Jul. 21, 1987 and U.S. Pat. No. 4,907,591, issued Mar. 13, 1990. As will be appreciated from a review of these patents, such devices in some instances may also be manually operated and are sometimes controlled from a location remote from the point of manipulation.

Figure 2:
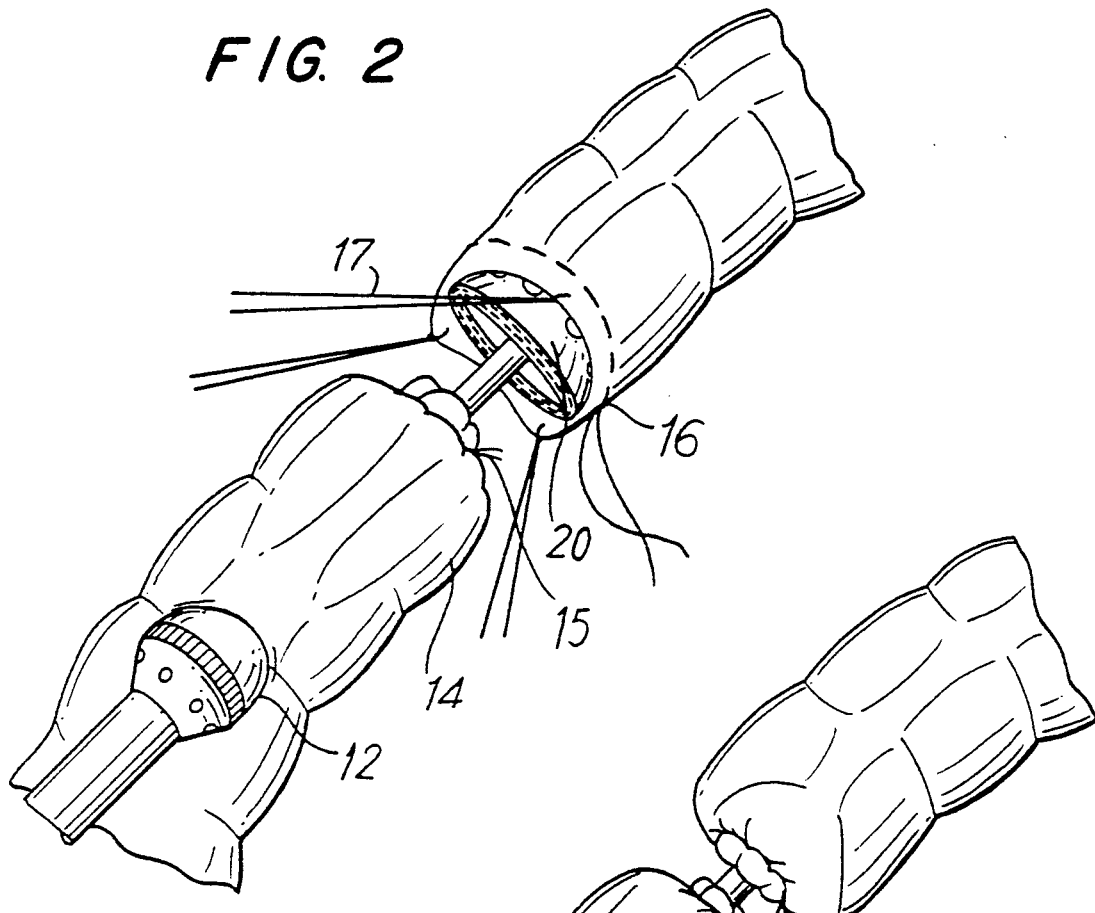
FIG. 2 is a perspective view of the apparatus of FIG. 1 illustrating the purse string procedure for securing tubular body portions in the form of sections of colon, in position for attaching the sections.

The apparatus 10 may be inserted into the tubular organs by a surgically provided opening shown at 12 in FIG. 2. Both ends 14, 16 of the intestinal organ are respectively temporarily secured to the fastener part 18 positioned within the colon end portion 14, and the anvil part 20 positioned within the colon end portion 16 opposite the tubular colon end 14. Purse string stitches 15 and 17 are included into the ends 14, 16 as shown by known procedures.

Figure 3:
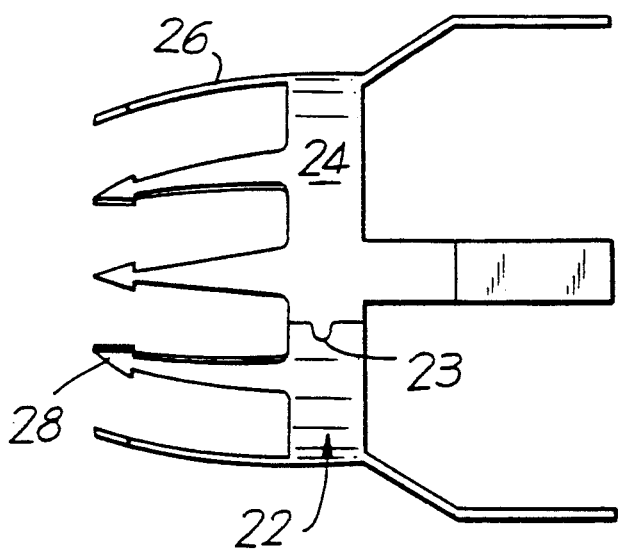
FIG. 3 is a plan view of a barbed apparatus for temporarily securing tubular body portions in position on the fastener part of an apparatus of the type shown in FIG. 1 for fastening procedure.
Figure 4:
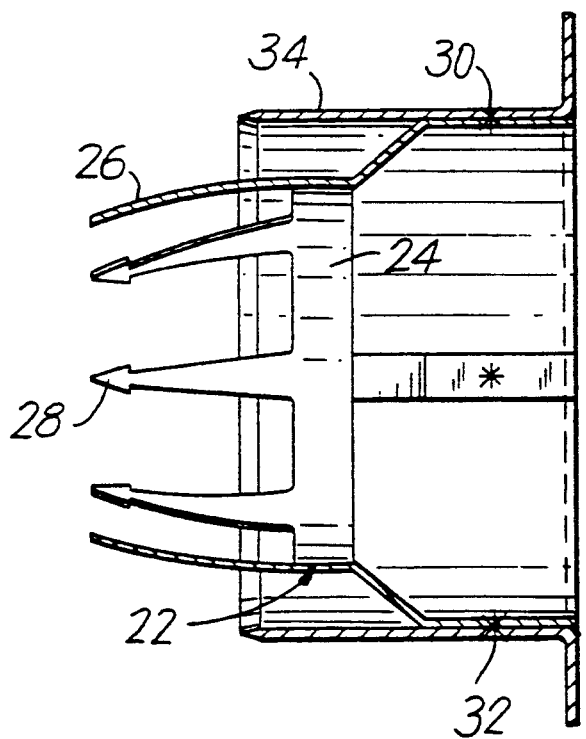
FIG. 4 is an elevational view, partially in cross-section, of combination of the barbed apparatus of FIG. 3 and a circular knife to secure for attachment procedure and to cut the excess tubular body portions after the attachment is completed on an apparatus of the type shown in FIG. 1.
Figure 5:
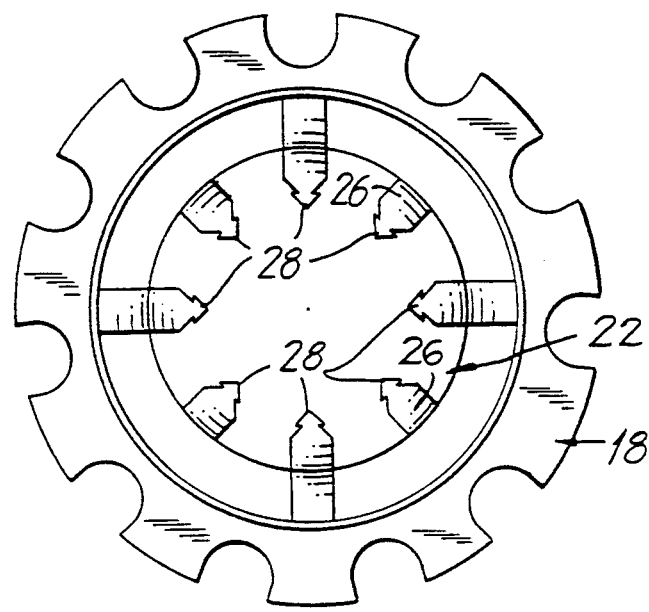
FIG. 5 is an axial view of the barbed apparatus shown in FIG. 4 mounted on a staple holding component of an apparatus of the type shown in FIG. 1.
Figure 6:
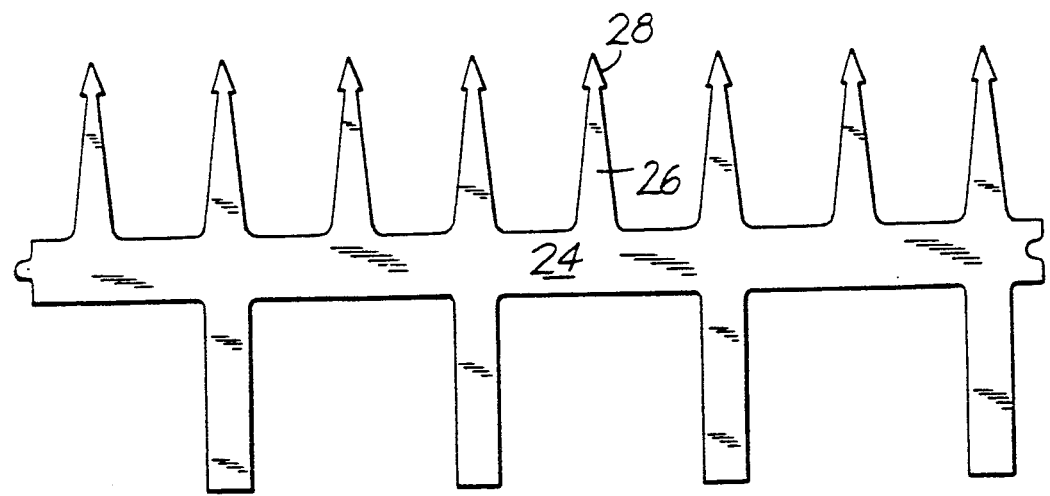
FIG. 6 is a plan view of a blank form of the barbed apparatus of FIG. 4 prior to formation and attachment to the knife.
Figure 11:
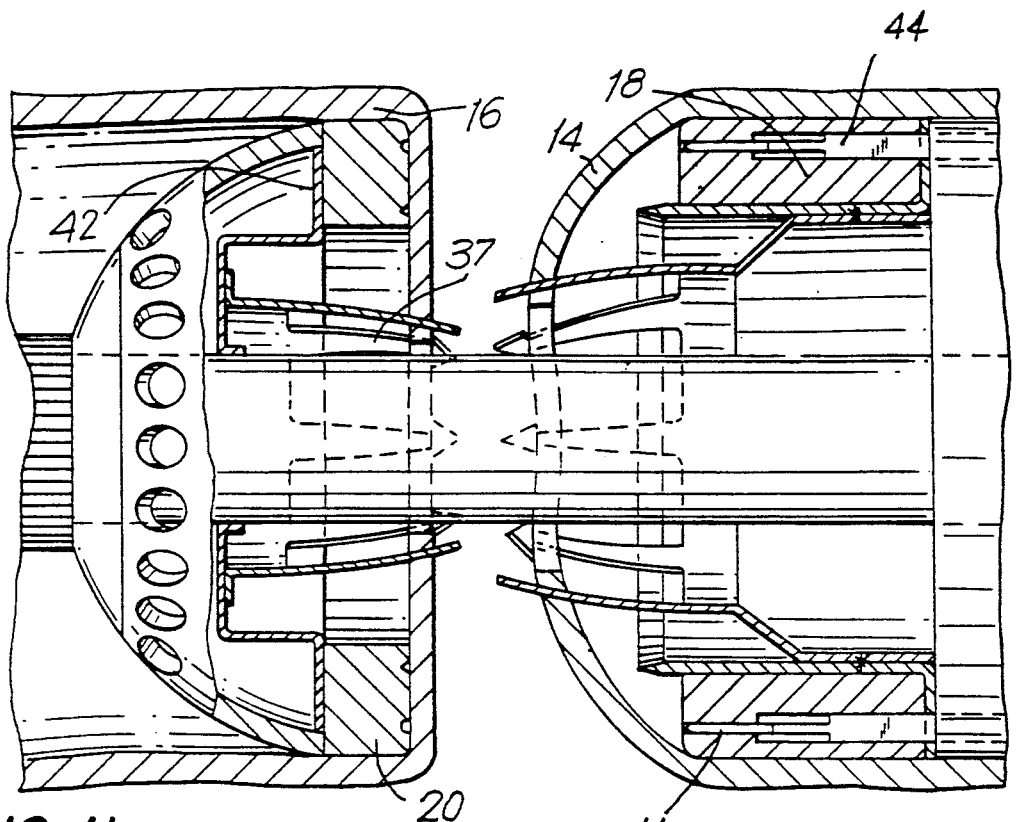
FIG. 11 is a side elevational partial cross-sectional view of an apparatus of the type shown in FIG. 1 with a barbed apparatus of the type shown in FIG. 4 in position on the fastening portion, and a barbed apparatus of the type shown in FIG. 7 in position on the anvil component, with the two components separated and with the end portions of the open body organs secured on the barbs for permanent attachment with staples.

Referring now to FIG. 3, there is illustrated a circular crown-like structure 22 having a circular annular shaped base 24 which includes a plurality of elongated members 26 having barbed tips 28. The crown-like structure is folded upon itself and attached by spot weld 23 as shown. Further, the crown-like structure is attached by spot welds 30 and 32 to the circular knife 34 as shown in FIG. 4 and is attached to the staple component 18 of the apparatus in concentric fashion with the circular array of staples in the apparatus as shown in FIGS. 5 and 11. Prior to formation, the crown-like structure is preferably stamped or otherwise formed from a single piece of 300 series stainless steel plate member, ¾ hardness, as shown in FIG. 6, with a plurality of elongated barbed members formed at the fine ends of elongated members. In the crown-like member shown in FIG. 6, there are eight such barbed elongated members which are thereafter cold worked to an inwardly shaped arcuate configuration as shown in FIG. 4. The stainless steel plate will have resilient properties which will assist in temporarily securing the colon ends as will be described. Other alternative metal plate material may be utilized within the context of the present disclosure.

Figure 7:
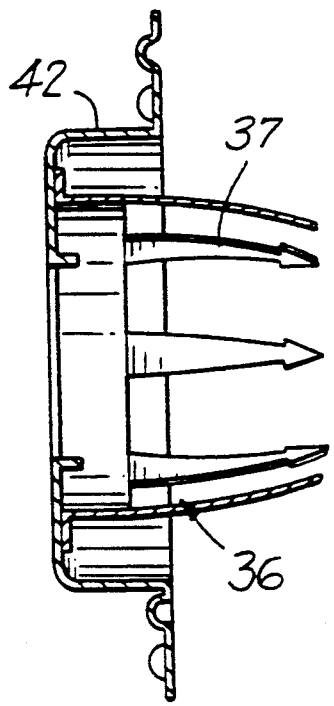
FIG. 7 is a side view, partially in cross-section, of a barbed apparatus for attachment to the anvil (or closure) portion of an apparatus of the type shown in FIG. 1.
Figure 8:
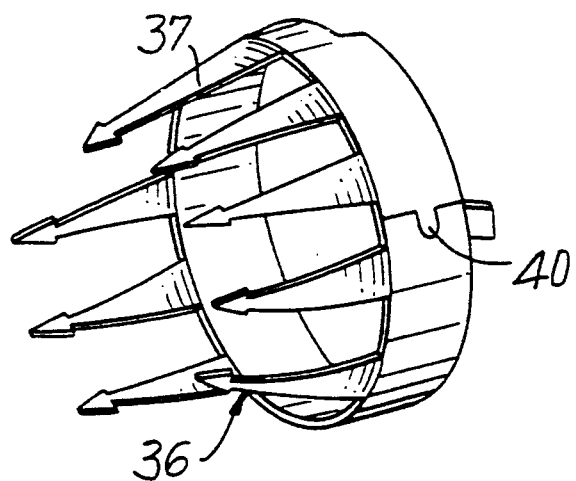
FIG. 8 is a perspective view of the barbed apparatus of FIG. 7.
Figure 9:
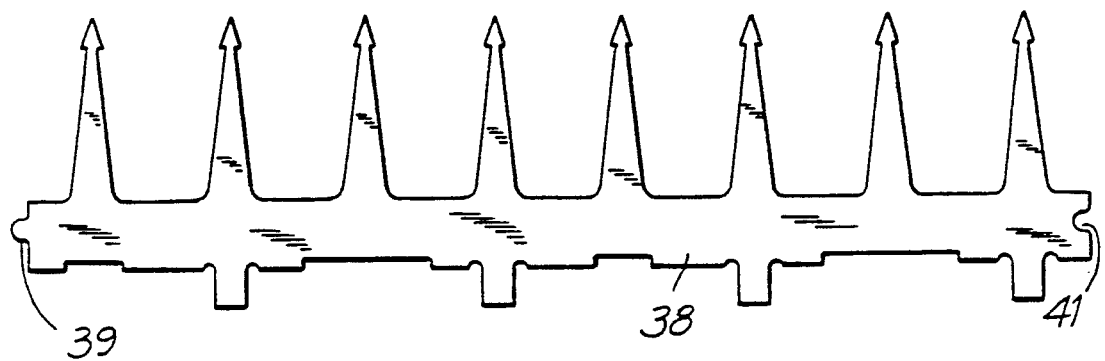
FIG. 9 is a plan view of a blank form of the barbed apparatus of FIG. 7 prior to assembly for attachment to an anvil or closure portion of an apparatus of the type shown in FIG. 1.
Figure 10:
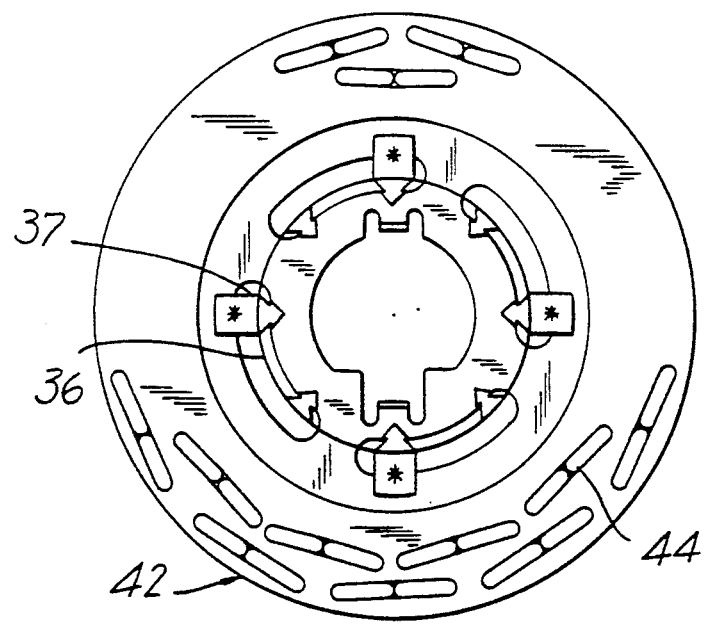
FIG. 10 is an axial view of the barbed apparatus of FIG. 7 mounted on an anvil of an apparatus of the type shown in FIG. 1.

Referring now to FIG. 7, the barbed crown-like member for attachment to the anvil (or closure end) of the fastening apparatus is shown. A crown like member 36 has barbed members 37 formed from a similar stamping 38 shown in FIG. 9, and of the same material. The member is arranged in a circular formation. The two ends are attached as by spot welding at 40 as shown in FIG. 8 to retain the annular shape, and the crown-like formation is attached to a mounting support member 42 shown in FIG. 7, which is utilized to mount the crown-like member to the anvil portion of the stapler or fastener apparatus concentrically with the staples as shown in FIG. 11. FIG. 8 shows the crown-like formation in perspective view. FIG. 10 is an end view of the device shown in FIG. 7 taken along lines 10-10.

Figure 12:
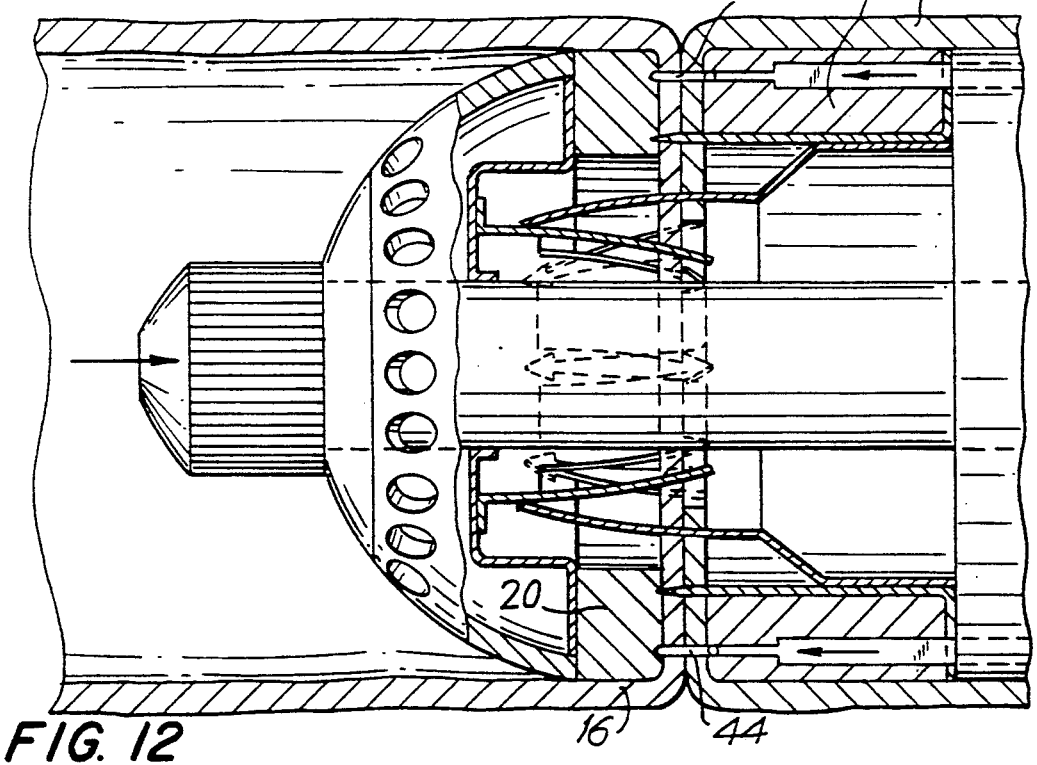
FIG. 12 is a side elevational partial cross-sectional view of the apparatus shown in FIG. 11 with the stapling component and the anvil component brought together for applying staples to attach the end portions of the organ.

It will be appreciated from FIG. 11, that the crown-like formation of the securement device on the anvil (or closure) side is lesser in diameter than the device on the stapler (or fastener) side to facilitate overlapping the devices as in FIG. 12 for stapling the colon ends.

In operation, the apparatus 10 (or manual stapler or fastener) has the crown-like member installed in position through a surgical opening 29 as shown in FIG. 11. This apparatus is inserted into the colon as shown in FIG. 2, and the respective colon end is stretched over the anvil and the fastening portion of the apparatus. Temporary securement of the colon ends is accomplished by hooking the end portions of the colon over the barbed members 26, 37, such that the members secure the colon ends in position in similar positions as was accomplished by the purse string. However, the securement is accomplished in relatively short time, with little trauma to the patient or the tissue. Further, the resilient property of the elongated spear-like members facilitates even quicker attachment by permitting similar flexibility in the manipulation and movements as is provided by the elasticity of the colon. Additionally, the "double hook" of the three pointed arrow-head "snagger" shape of the tip of the spear-like member facilitates even faster attachment with greater success in temporary securement.

After temporary securement is complete, the anvil and fastening members of the apparatus are brought together and staples 44 are fired into the overlapped end portions of the colon ends. At the same time, the knife 34 of the barbed device shown in FIG. 4 cuts the excess overlapped tissue presently positioned in the inner portion of the attached colon sections as the interface, and those inner portions remain on the barbed ends for easy removal from the colon with the stapling apparatus. Thus the colon is cleared to permit matter to pass through the organ. Thus, the attachment of the end portions of the colon is accomplished more quickly than the procedure utilizing purse string securement. Additionally, the quick snagging action of the uniformly distributed barbed tips facilitates uniform and even positioning of the colon end portions with a minimum of wrinkles or discontinuities, as well as ready removal of the inner portions of the intestine after the stapling procedure.

The barbed device of the present invention may be utilized with a stapler or a two-part fastener (i.e. absorbable fastener) apparatus for attaching tubular body portions such as intestinal organs or the like. Also, the barbed device may be utilized in connection with a temporary fixture or jig to secure the end portions of the organ in position for attachment by other means such as sutures. Further, it will be appreciated that attachment of all body parts such as intestines, esophagus, etc., tubular and non-tubular are applicable.

What is claimed is:

1. In combination with an apparatus for performing circular anastomosis of first and second body portions wherein a first fastening member is adapted to support a first tubular body portion and a second fastening member is adapted to cooperate with said first fastening member to attach the first tubular body portion to the second body portion which comprises:
   a) a body tissue holding member positionable on said first fastening member and having a plurality of sharp tipped members positioned and oriented to pierce portions of said first body portion in a manner to secure said first body portion in position for attachment to said second body portion.

2. In an apparatus for performing circular anastomosis at a location remote from the location at which the instrument is manipulated which comprises:
   a) an elongated member having opposite distal and proximal ends;
   b) means located at the distal end of said elongated member for performing the surgical fastening procedure, said fastening means having proximal and distal fastening components arranged to be positioned within the respective opposite end portions of generally tubular shaped body portions to be fastened and to cooperate with each other for applying a circular array of staples or fasteners for fastening the generally tubular body portions;
   c) means connected to said distal fastening member in general concentric alignment therewith and having a plurality of sharp tipped members facing the proximal direction and positioned in a generally circular array, said sharp tipped members adapted to penetrate and secure for fastening a tubular body portion positioned about said distal fastening member to maintain said body portion in position for circular fastening to the opposite body portion;
   d) means connected to said proximal fastening member in general concentric alignment therewith and having a plurality of sharp tipped members facing the distal direction and positioned in a generally circular array, said sharp tipped members adapted to penetrate and secure for fastening, a tubular body portion positioned about said proximal fastening member to maintain said body portion in position for circular fastening to the opposite body portion.

3. The apparatus according to claim 2 wherein said apparatus for attaching the tubular body portions is a surgical stapler.

4. The apparatus according to claim 3 wherein said first member is a crown-like member having a plurality of barbed elongated members extending from a generally annular shaped base member.

5. The apparatus according to claim 4 wherein said crown-like member is stamped from sheet metal.

6. The apparatus according to claim 5 wherein said sheet metal is stainless steel.

7. The apparatus according to claim 6 wherein said stainless steel is resilient.

8. The apparatus according to claim 7 wherein said second member is a crown-like member having a plurality of barbed elongated members extending from a generally circular shaped base member.

9. The apparatus according to claim 8 wherein said crown-like member is stamped from sheet metal.

10. The apparatus according to claim 9 wherein said sheet metal is stainless steel.

11. The apparatus according to claim 10 wherein said stainless steel is resilient.

12. The apparatus according to claim 4 wherein said crown-like member includes eight elongated members each having a spear-like tip.

13. The apparatus according to claim 12 wherein each spear-like tip has three points.

14. The apparatus according to claim 12 wherein said spear-like members are arranged in a circular array and are equally distributed to firmly and uniformly secure the body organ for fastening procedure.

15. The apparatus according to claim 8 wherein said crown-like member includes eight elongated members each having a spear-like tip.

16. The apparatus according to claim 15 wherein each spear-like tip has three points.

17. The apparatus according to claim 13 wherein said spear-like members are arranged in a circular array and are equally distributed to firmly and uniformly secure the body organ for fastening procedure.

18. The apparatus according to claim 12 wherein each spear like tip has a sharp pointed tip and at least two trailing sharp edges.

19. The apparatus according to claim 15 wherein each spear like tip has a sharp pointed tip and at least two trailing sharp edges.

20. The apparatus according to claim 14 wherein said spear-like members are generally arcuate in size with the concave side facing the longitudinal axis of said crown-like member.

21. The apparatus according to claim 17 wherein said spear-like members are generally arcuate in size with the concave side facing the longitudinal axis of said crown-like member.

22. An apparatus for temporarily securing open end portions of a tubular body organ for attachment to each other wherein a first proximal member is inserted into one tubular body portion and a distal member is inserted into the other tubular body portion for positioning in relative opposite positions for attachment to each other, the improvement which comprises:
   a) a first tissue holding member positionable on said proximal member and having a plurality of generally sharp tipped elongated members facing distally for piercing an end portion of a first tubular body organ to retain the tubular body organ in fixed position for attachment to the other tubular body organ; and b) a second tissue holding member positionable on said distal member and having a plurality of generally sharp tipped elongated members facing proximally for piercing an end portion of a second tubular body portion to retain the tubular body portion in fixed position opposite the first tubular body portion end portion for attachment to each other.

23. In combination with an apparatus for performing circular anastomosis of opposed open end portions of generally tubular shaped body portions wherein a proximal fastening member is adapted to support an open tubular body portion and a distal member is adapted to cooperate with said proximal fastening member to apply fastener means to attach the end portions of the tubular members, the improvement which comprises:

a) a first member positionable on said proximal member and having a plurality of generally sharp tipped members facing distally for attaching an end portion of the tubular body portion to retain the body portion in position for fastening to the other body portion; and b) a second member positionable on said cooperating distal fastening member and having a plurality of sharp tipped members facing the proximal direction for securing an end portion of the other tubular body portion to retain the body portion in position for fastening to said first body portion.

24. In combination with an apparatus for performing circular anastomosis of first and second body portions wherein a proximal fastening member is adapted to support a first body portion and a distal member is adapted to cooperate with said proximal fastening member to attach the body portions by circular anastomosis, the improvement which comprises:

a) a first member positionable on said proximal member and having a plurality of generally sharp tipped members facing distally for securing the first body portion to retain the body portion in position for fastening to the second body portion; and b) a second member positionable on said cooperating distal fastening member and having a plurality of sharp tipped members facing the proximal direction for securing the second body portion to retain the body portion in position for attachment to the first body portion by circular anastomosis.

25. The apparatus according to claim 24 further comprising circular knife means to cut inner excess portions of tissue to complete the circular anastomosis.

26. A method for securement of a first body portion for attachment to a second body portion wherein a first fastener member and a second fastener member are adapted to cooperate with each other to attach the body portions by circular anastomosis, comprising:

a) positioning a crown-like member on a first of said fastener members to secure the body portion thereon for attachment to the other body portion, said crown-like member having an annular base member and a plurality of sharp spear-like members extending in an annular array from said base member toward said other fastening member and generally parallel to the central longitudinal axis of said fastening members;

b) positioning said body portion over said first fastening member and folding an end portion over said crown-like member in a manner to cause said sharp spear-like members to pierce the body portion to secure the body portion in position for attachment to the second body portion; and c) attaching the first body portion to the second body portion.

27. The method according to claim 26 wherein said first body portion is tubular.

28. The method according to claim 27 wherein said second body portion is tubular.

29. A method for securement of generally tubular hollow body parts in preparation for attachment by staples, two part fasteners, sutures or the like comprising:

a) providing a first crown-like member having an annular base member and a plurality of sharp spear-like members extending in an annular array from said base member and generally parallel to a central longitudinal axis extending therethrough;

b) mounting said crown-like member and support means and inserting said support means into an end portion of a first hollow body part;

c) providing a second a crown-like member on said support means, said second member having an annular base member and a plurality of sharp spear-like members extending in an annular array from said base member and generally parallel to said central longitudinal axis, said spear-like members facing a direction opposite the spear-like members of said first crown-like member;

d) inserting said second crown-like member into the opposite open end portion of a second hollow body part to be attached to the first hollow body part;

e) folding the end portion of said first hollow body part over said sharp end portions of said spear-like members of said first crown-like member to cause said spear-like members to penetrate marginal end portions of the hollow body part in a manner to secure the marginal end portion of the hollow part in position to facilitate permanent attachment to the second hollow body part; and f) folding the end portion of the second hollow body part over said sharp end portions of said spear-like members of said second crown-like member to cause said spear-like members to penetrate marginal end portions of the second hollow body portion in a manner to secure the marginal end portion thereof to facilitate permanent attachment to the first hollow body part.

30. In an anvil for providing closure to staples applied by a circular staple applying apparatus, the staples being applied in a circular array and the anvil having a plurality of lands correspondingly positioned to receive and close the staples, the improvement in combination therewith which comprises a crown-like member having an annular base member formed of a resilient sheet steel and having a plurality of elongated sharp spear-like members extending from said annular base member and integral therewith, said resilient spear-like members being generally curved inwardly toward the anvil longitudinal axis from the base member to the sharp tips at the free ends thereof to facilitate piercing free end portions of a hollow body part in which said crown-like member is inserted for securing the body part in position in overlapping relation to the anvil staple closure lands for permanent staple attachment of the hollow body part to an opposite body part.

* * * * *

UNITED STATES PATENT AND TRADEMARK OFFICE
CERTIFICATE OF CORRECTION

PATENT NO. : 5,122,156

DATED : June 16, 1992

INVENTOR(S) : Richard N. Granger et al.

It is certified that error appears in the above-identified patent and that said Letters Patent is hereby corrected as shown below:

Title page, item [56] under "References Cited, U.S. PATENT DOCUMENTS" add the following:

FOREIGN PATENT DOCUMENTS 1509052          9/1989          Soviet Union

At Column 3, line 63, "a second a crown-like" should read --a second crown-like--.

Figure 2A:
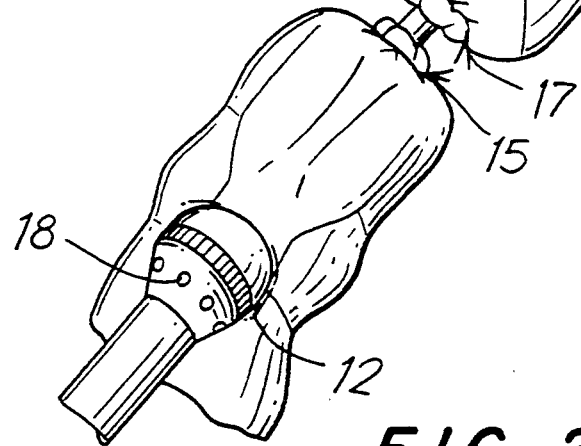

At Column 4, line 53, insert --Fig. 2A is a view similar to Fig. 2 after the purse string is secured around the colon sections.--

At Column 5, line 59, "Fig. 2" should read --Figs. 2 and 2A--.

At Column 6, line 36, delete "taken along lines 10-10".

UNITED STATES PATENT AND TRADEMARK OFFICE
CERTIFICATE OF CORRECTION

PATENT NO. : 5,122,156
DATED : June 16, 1992
INVENTOR(S) : Richard N. Granger et al It is certified that error appears in the above-indentified patent and that said Letters Patent is hereby corrected as shown below:

At Column 6, line 44, "29 as shown in Fig. 11" should read --of the type shown at 12 in Fig. 2--.
Col. 10,
In claim 29, line 13, "a second a crown-like" should read --a second crown-like--.

Signed and Sealed this

Fourteenth Day of September, 1993

Attest:

BRUCE LEHMAN

Attesting Officer    Commissioner of Patents and Trademarks